US 6,528,232 B1

(12) United States Patent
Maeda et al.

(10) Patent No.: US 6,528,232 B1
(45) Date of Patent: Mar. 4, 2003

(54) SULFONIUM SALT COMPOUND, PHOTORESIST COMPOSITION AND METHOD FOR PATTERNING BY EMPLOYING SAME

(75) Inventors: Katsumi Maeda, Tokyo (JP); Shigeyuki Iwasa, Tokyo (JP); Kaichiro Nakano, Tokyo (JP); Etsuo Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 09/699,368

(22) Filed: Oct. 31, 2000

(30) Foreign Application Priority Data

Nov. 1, 1999 (JP) .............................. 11-310827
Feb. 10, 2000 (JP) ........................ 2000-33652

(51) Int. Cl.$^7$ .............................................. G03F 7/004
(52) U.S. Cl. .................. 430/270.1; 430/311; 430/313; 430/317; 430/328; 430/343; 568/17; 568/28; 568/35; 568/77
(58) Field of Search ............................ 430/270.1, 311, 430/313, 317, 328, 343; 568/18, 28, 35, 77

(56) References Cited

U.S. PATENT DOCUMENTS

| | | | | |
|---|---|---|---|---|
| 5,326,675 A | * | 7/1994 | Niki et al. .................. | 430/326 |
| 5,573,890 A | | 11/1996 | Spence ........................ | 430/311 |
| 5,748,656 A | * | 5/1998 | Watson et al. ................. | 372/35 |
| 5,766,804 A | | 6/1998 | Spence ........................... | 430/5 |
| 5,766,806 A | | 6/1998 | Spence ........................... | 430/5 |
| 5,776,657 A | * | 7/1998 | Schadeli et al. ......... | 430/281.1 |
| 6,063,549 A | * | 5/2000 | Schadeli et al. ............ | 430/325 |
| 6,071,670 A | * | 6/2000 | Ushirogouchi et al. .. | 430/270.1 |
| 6,074,801 A | * | 6/2000 | Iwasa et al. ............. | 430/270.1 |
| 6,110,639 A | * | 8/2000 | Masuda et al. .......... | 430/270.1 |
| 6,214,517 B1 | * | 4/2001 | Sato et al. ............... | 430/270.1 |
| 6,348,297 B1 | * | 2/2002 | Uetani et al. ............. | 430/270.1 |

OTHER PUBLICATIONS

Hartke et al, On the Reaction of Silyl Enol Ethers with Activated Sulfoxides;Liebigs Ann. Chemistry, vol. 3, pp. 225–230 (1988).*

Maycock et al, Photochemical Reactions of Phenacyl– and Benzylsulfonium Salts;Journal of Organic Chemistry, vol. 35, pp. 2532–2538 (1970).*

Crivello et al, Long–Wavelength–Absorbing Dialkylphenacylsulfonium Salt Photoinitiators:Synthesis and Photoinduced Cationic Polymerization; Journal of Polymer Science:Part A:Polymer Chemistry, vol. 38, 1433–1442 (2000).*

* cited by examiner

*Primary Examiner*—Janet Baxter
*Assistant Examiner*—Amanda C. Walke
(74) *Attorney, Agent, or Firm*—Young & Thompson

(57) ABSTRACT

A sulfonium salt compound designated by a general formula (I), a photoresist composition containing the sulfonium salt compound and a method for patterning by employing the sulfonium salt compound. In the general formula (I), $R^1$ and $R^2$ are independently selected from the group consisting of a linear alkyl group, a branched alkyl group, a monocyclic alkyl group and a cross-linked cyclic alkyl group, or $R^1$ and $R^2$ having the saturated alkyl group are linked to each other forming a ring or $R^1$ and $R^2$ are linked to each other forming a ring having a substituted oxo group, $R^3$, $R^4$, $R^5$ and $R^6$ are independently selected from the group consisting of a hydrogen atom, a halogen atom, an alkyl group and an alkoxy group having 1 to 4 carbon atoms, X is selected from the group consisting of —$CH_2$—, —$C_2H_4$— and —$OCH_2$— (wherein an oxy group is bonded to a benzene ring), and $Y^-$ is a counter ion (I)

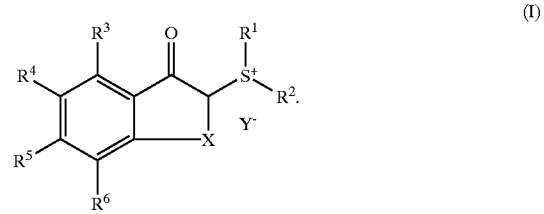

7 Claims, No Drawings

SULFONIUM SALT COMPOUND, PHOTORESIST COMPOSITION AND METHOD FOR PATTERNING BY EMPLOYING SAME

BACKGROUND OF THE INVENTION (a) Field of the Invention

The present invention relates to a novel sulfonium salt compound employable as a photo-acid generator for a chemically amplified photoresist material, a chemically amplified photoresist composition using the novel sulfonium salt compound as the photo-acid generator, and a method for patterning by using the photoresist composition. More concretely, the present invention relates to the novel sulfonium salt compound suitably used as the photo-acid generator for the chemically amplified photoresist material having an exposing wavelength in a range from a far ultraviolet ray to a vacuum ultraviolet ray having a wavelength between 130 nm and 220 nm.

(b) Description of the Related Art

Higher density, higher integration or higher speed is required in a highly integrated circuit element represented by a semiconductor device such as a DRAM (dynamic random access memory). Accompanied thereby, the establishment of the fine processing technology in a range of half-micron order, for example, the photolithographic technology for forming fine patterns is required more and more stringently in the field of manufacturing electronic devices.

A process of implementing the fine patterns in the photolithographic technology includes the shortening of a wavelength of an exposing ray used in the formation of the patterned resist. Generally, the degree of optical resolution (R) can be represented by the Rayleighs equation, that is, $R = k \cdot \lambda / NA$ (wherein $\lambda$ is a wavelength of an exposing ray, NA is numerical aperture and "k" is a process factor). In order to progress the formation of fine patterns, the higher optical resolution is required in the optical system used therein, or the wavelength "$\lambda$" of the exposing ray is shortened for reducing the degree of the resolution "R" of the optical system.

In the manufacture of a DRAM of 256 megabits, for example, the degree of resolution of line-and-space having the minimum pattern dimension of 0.22 $\mu$m is required, and a KrF excimer laser (wavelength: 248 nm) is used as a light source. In the manufacture of an advanced DRAM of 1 gigabit or more, the patterning dimension becomes 0.15 $\mu$m or less requiring the finer processing technique, and an ArF excimer laser (wavelength: 193 nm) and an $F_2$ excimer laser (wavelength: 157 nm) having a shorter wavelength ray (a far ultraviolet ray and a vacuum ultraviolet ray) are efficiently utilized and required. Currently, the lithography using the ArF excimer laser is extensively researched [refer to Journal of Photopolymer Science and Technology, vol.9, no.3, p.387 to 397 (1996)].

In the use of the ArF excimer laser and the $F_2$ excimer laser, the higher sensitivity is requested in the development of resist for exposure in addition to the higher resolution responding to the fine processing dimension because the lifetime of a gas used in these lasers is short and the damage of a lens generated by a laser ray is large. A chemically amplified photoresist is well known utilizing a photo-acid generator as a sensitized material for obtaining the higher sensitivity of the resist. A representative example is described in JP-A-2(1990)-27660 showing a resist formed by a combination of poly(p-tert-butoxy carbonyloxy-α-methylstyrene) and triphenylsulfonium hexafluoro-arsenate acting as a photo-acid generator. The chemically amplified photoresist is currently used for the KrF excimer laser [for example, refer to Hiroshi Ito and C. Grantwilson, American Chemical Society Symposium Series, vol.242, p.11 to 23 (1984)].

The chemically amplified photoresist characteristically generates a protonic acid from the photo-acid generator contained therein by means of irradiation of light, and the protonic acid reacts with resist resin under existence of an acid catalyst by a thermal treatment after exposure. By using the acid catalysis, the considerably higher sensitivity can be attained compared with a conventional resist having a photoreaction efficiency (reaction per one photon) of 1 or less. Most of the resists currently developed are chemically amplified ones. An example of the photo-acid generator currently used includes a triphenyl- sulfonium salt derivative developed by J. V. Crivello described in J. Org.Chem., vol.43, no.15, p.3055 to 3058 (1978).

A representative example of the photo-acid generator currently used in the chemically amplified resist for the ArF excimer laser already proposed is the triphenylsulfonium salt derivative [refer to, for example, Nozaki, et al., Journal of Photopolymer Science and Technology, vol.10, no.4, p.545 to 550 (1997) or Yamachika, et al., Journal of Photopolymer Science and Technology, vol.12, no.4, p.553 to 560 (1999)]. Since, however, these triphenylsulfonium salt derivatives strongly absorb light having a wavelength of 220 nm or less, the transparency of the resist is reduced to lower the resolution when the triphenylsulfonium salt derivative is used as the photo-acid generator [refer to, for example, Takuya Naito, 8 th Optical Reaction and Electronic Material Research Course, Lecture Brief, p.16 to 18 (1999)].

Accordingly, one of the technical problems currently researched in the development of the resist material suitable for exposure to a light having a wavelength of 130 to 220 nm representatively used in the ArF excimer laser is the development of the photo-acid generator having a higher photoreaction efficiency (photo-acid generation efficiency) and a higher transparency to an ultraviolet ray of a wavelength of 220 nm or less.

SUMMARY OF THE INVENTION

In view of the foregoing, an object of the present invention is to provide a novel photo-acid generator or a novel sulfonium salt compound utilized in a chemically amplified resist material suitable for a light having a wavelength of 130 to 220 nm representatively used in the ArF excimer laser, and more in detail, to the novel photo-acid generator having a higher transparency to an ultraviolet ray of a wavelength of 220 nm or less and a higher photoreaction efficiency (photo-acid generation efficiency).

Another object of the present invention is to provide a chemically amplified resist composition containing the novel photo-acid generator.

A further object of the present invention is to provide a method for patterning by using the photoresist composition.

The present invention provides, in a first aspect thereof, a sulfonium salt compound designated by a general formula (I),

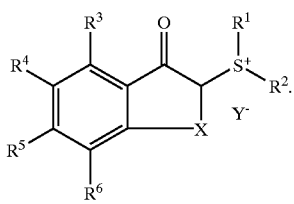

(I)

wherein $R^1$ and $R^2$ are independently selected from the group consisting of a linear alkyl group, a branched alkyl group, a monocyclic alkyl group and a cross-linked cyclic alkyl group, or $R^1$ and $R^2$ having the saturated alkyl group are linked to each other forming a ring or $R^1$ and $R^2$ are linked to each other forming a ring having a substituted oxo group, $R^3$, $R^4$, $R^5$ and $R^6$ are independently selected from the group consisting of a hydrogen atom, a halogen atom, an alkyl group and an alkoxy group having 1 to 4 carbon atoms, X is selected from the group consisting of —$CH_2$—, —$C_2H_4$— and —$OCH_2$— (wherein an oxy group is bonded to a benzene ring), and $Y^-$ is a counter ion.

The present invention provides, in a second aspect thereof, a method including the steps of: forming a photoresist layer by application of the sulfonium salt compound of the present invention as described above as a positive photoresist material or a negative photoresist material on an underlying layer to be patterned; transferring a desired pattern to the photoresist film on a photoresist composition by exposing the photoresist layer to light having a wavelength between 130 and 220 nm; baking the photoresist layer: and developing the photoresist layer to form a photoresist pattern.

In accordance with the first and the second aspects of the present invention, the sulfonium salt compound having 1-oxoindan-2-yl group or a similar group can be used as a photo-acid generator which is excellent in transparency in a range from a far ultraviolet ray to a vacuum ultraviolet ray having a wavelength between 130 nm and 220 nm. Accordingly, the photoresist composition using the sulfonium salt compound of the present invention as the photo-acid generator has a higher sensitivity and a higher resolution with respect to the exposure light in the range from the far ultraviolet ray to the vacuum ultraviolet ray having a wavelength between 130 nm and 220 nm, thereby facilitating the fine pattern formation in the manufacture of a semiconductor device.

The above and other objects, features and advantages of the present invention will be more apparent from the following description. PREFERRED EMBODIMENTS OF THE INVENTION Now, the present invention is more specifically described.

After producing various novel sulfonium salt compounds and examining the properties thereof, the present inventors have found that a sulfonium salt compound of the following general formula (I) containing, in place of various phenyl groups in a conventional triphenyl sulfonium salt derivative, 1-oxoindan-2-yl group, various substituted 1-oxoindan-2-yl groups, 1-tetralone-2-yl group, various substituted 1-tetralone-2-yl groups, 4-chromanone-2-yl group or various substituted 4-chromanone-2-yl groups has a higher photoreaction efficiency (photo-acid generation efficiency) and an excellent transparency with respect to an ultraviolet ray having a wavelength of 220 nm or less, and have reached to the present invention.

The sulfonium salt compound of the present invention has a structure specified in the above general formula (I) and includes a cyclic group selected from the group consisting of 1-oxoindan-2-yl group, various substituted 1-oxoindan-2-yl groups, 1-tetralon-2-yl group, various substituted 1-tetralon-2-yl groups, 4-chromanon-2-yl group and various substituted 4-chromanon-2-yl groups, and various alkyl groups designated by $R^1$ and $R^2$. The exposure is conducted by the absorption originated from the cyclic groups. Since the other absorption originated from the remaining $R^1$ and $R^2$ groups is quite small in the wavelength range between 130 and 220 nm, the sulfonium salt compound of the present invention exhibits the excellent transparency with respect to the ultraviolet ray having the wavelength of 220 nm or less. In addition, a production yield of a protonic acid ($H^+$—$Y^-$) generated during the exposure is maintained to be high. The reaction occurring in the chemically amplified photoresist material or the acid catalyzed reaction in the resist resin catalyzed by the protonic acid ($H^+$—$Y^-$) is unchanged. The excellent transparency of the sulfonium salt compound of the present invention with respect to the ultraviolet ray having the wavelength of 220 nm or less allows the exposure light to uniformly penetrate deep in the resist film. Accordingly, the protonic acid is generated uniformly in a direction of depth of the film to provide a higher resolution during the transfer of the pattern.

In the sulfonium salt compound of the present invention, the substituted groups $R^1$ and $R^2$ in the sulfonium group may be independently a linear alkyl group such as methyl group, ethyl group, propyl group, butyl group, pentyl group, hexyl group and heptyl group, a branched alkyl group such as isopropyl group, isobutyl group and tert-butyl group, a monocyclic cycloalkyl group such as cyclopentyl group, cyclohexyl group, cycloheptyl group and cyclooctyl group, and a bridged alkyl group such as norbornyl group, isobornyl group, adamantyl group, tricyclodecyl group and tetracyclododecyl group. In addition, $R^1$ and $R^2$ may bind to each other to form a ring or a bivalent group "—$R^1$—$R^2$—" containing the above carbon skeletons. An example of the bivalent group includes an alkylene group such as tetramethylene group and pentamethylene group and an oxoalkylene group such as 2-oxotetramethylene group and 3-oxopentamethylene group prepared by oxo-substitution of the alkylene group.

The ring formed by the bivalent group "—$R^1$—$R^2$—" with the sulfur "S" atom may be 4 to 8-membered ring, more preferably 5 or 6-membered ring. A preferred group is not restricted to those mentioned above.

An example of $R^3$ to $R^6$ in the cyclic group of the general formula (I) or the 1-oxoindan-2-yl group, the 1-tetralone-2-yl group or the 4-chromanone-2-yl group includes a hydrogen atom, a halogen atom, an alkyl group having 1 to 4 carbon atoms, and an alkoxy group having 1 to 4 carbon atoms. The halogen atom includes a fluorine atom, a chlorine atom, a bromine atom and an iodine atom. The alkyl group includes methyl group, ethyl group, propyl group, isopropyl group, butyl group, isobutyl group and tert-butyl group. The alkoxy group includes methoxy group, ethoxy group and butoxy group. The preferable group for the $R^3$ to $R^6$ is not restricted thereto.

An example of the counter ion "$Y^-$" in the sulfonium salt compound of the general formula (I) is converted into the protonic acid ($H^+$—$Y^-$) during the exposure. Actual catalysis is determined according to the resist resin employed. Accordingly, the anionic component "$Y^-$" conventionally used in this kind of photo-acid generator can be selected in accordance with the resist resin. More concretely, a suitable example thereof includes perfluoroalkylsulfonate ion designated by a general formula (II) (wherein "m" is a positive integer from 1 to 9)

$$C_{mF_{2m+1}}SO_3^-  \quad (II)$$

such as $CF_3SO_3^-$ (trifluoromethanesulfonate ion), $C_4F_9SO_3^-$ (nonafluorobutanesulfonate ion) and $C_8F_{17}SO_3^-$ (heptadecafluorooctanesulfonate ion). The preferable perfluoroalkylsulfonate ion is not restricted thereto. A suitable example of the anionic component "Y⁻" further includes alkanesulfonate ion designated by a general formula (III) (wherein "k" is a positive integer from 1 to 9)

$$C_kH_{2k+1}SO_3^- \quad (III)$$

such as $CH_3SO_3^-$ (methanesulfonate ion), $C_2H_4SO_3^-$ (ethanesulfonate ion), $C_8H_{17}SO_3^-$ (1-octanesulfonate ion) and $C_9H_{19}SO_3^-$ (1-nonanesulfonate ion). The preferable alkanesulfonate ion is not restricted thereto.

A suitable example of the anionic component "Y⁻" further includes benzenesulfonate ion and alkylbenzenesulfonate ion which includes p-toluenesulfonate ion and xylenesulfonate ion. The preferable alkylbenzenesulfonate ion is not restricted thereto.

A suitable example of the anionic component "Y⁻" further includes fluorinated benzenesulfonate ion such as 4-fluorobenzenesulfonate ion and pentafluorobenzenesulfonate ion. The preferable fluorinated benzenesulfonate ion is not restricted thereto. A suitable example of the anionic component "Y⁻" further includes fluorinated alkylbenzenesulfonate ion such as 4-trifluoromethylbenzenesulfonate ion and 3,5-bis(trifluoromethyl)benzenesulfonate ion. The preferable fluorinated alkylbenzenesulfonate ion is not restricted thereto.

A suitable example of the anionic component "Y⁻", further includes a fluorinated ion such as $BF_4^-$ (tetrafluoroborate ion), $AsF_6^-$ (hexafluoroarsenate ion) $SbF_6^-$ (hexafluoroantimonate ion) and $PF_6^-$ (hexafluorophosphate ion), and a halogenated ion such as Br⁻ (bromine ion) and I⁻ (iodine ion). The preferable inorganic anion is not restricted thereto.

The counter ion represented by the "Y⁻" in the sulfonium salt compound is, as described above, converted into the protonic acid (H⁺—Y⁻) during the exposure. The catalysis by the protonic acid must be maintained, and the counter ion is preferably selected such that the protonic acid is not vaporized nor scattered during the baking after the exposure.

The photoresist composition of the present invention may be positive or negative. The composition is the chemically amplified resist, contains, as the main components, the sulfonium salt compound as the photo-acid generator, the resin used as the resist and a solvent for dissolving these components. In the negative photoresist, a crosslinking agent for promoting the insolubilization of the resin at the exposed portion may be added similar to the conventional negative photoresist.

In the photoresist composition of the present invention, the sulfonium salt compound represented by the general formula (I) is used as the photo-acid generator wherein a single compound or a plurality of mixed compounds may be used. In the chemically amplified resist, the photo-acid generator is added and mixed at a specified ratio with respect to the resin, and the solvent has a roll of uniformly dissolving the resin, the photo-acid generator and the other additives. The solvent is suitably selected for adjusting the viscosity of the photoresist composition for the purpose of making the applicability in a specified range. Ordinarily, 0.2 to 30 weight parts, preferably 1 to 15 weight parts of the sulfonium salt compound represented by the general formula (I) with respect to 100 weight parts of the whole photoresist composition excluding the solvent is appropriate. The sufficient sensitivity is obtained at 0.2 weight part or more, and the pattern formation can be easily conducted. The uniform applied film can be formed and the scum is hardly generated after the development at 30 weight parts or less. The weight parts of the sulfonium salt compound may be selected depending on the kind of the resist resin employed and the acid catalyst reactivity of the protonic acid formed from the sulfonium salt compound.

In the positive photoresist composition, the resin is suitably used which is highly transparent to the ray having the wavelength of the exposing ray in the range from the far ultraviolet ray to the vacuum ultraviolet ray having a wavelength between 130 nm and 220 nm and may be solubilized in an alkaline developing solution by the function of the acid. Ordinarily, 60 to 99.8 weight parts, preferably 75 to 99 weight parts of the resin with respect to 100 weight parts of the whole photoresist composition excluding the solvent is appropriate.

The resin preferably used in the positive photoresist composition of the present invention includes resins represented by the following general formulae (IV), (V), (VI) and (VII).

The resin having the general formula (IV) is described in JP-A-2000-26446, wherein $R^7$, $R^8$, $R^9$ and $R^{11}$ are hydrogen atom or methyl group, $R^{10}$ is a group decomposable by an acid, or a bridged cyclic hydrocarbon group having 7 to 13 carbon atoms and a group decomposable by an acid, $R^{12}$ is a hydrogen atom, a hydrocarbon group having 1 to 12 carbon atoms or a bridged cyclic hydrocarbon group having 7 to 13 carbon atoms and a carboxyl group, x, y and z are any numbers satisfying the relation of x+y+z=1, 0<x<1, 0<y<1 and 0<z<1, and the weight average molecular weight of the polymer is 2000 to 200000.

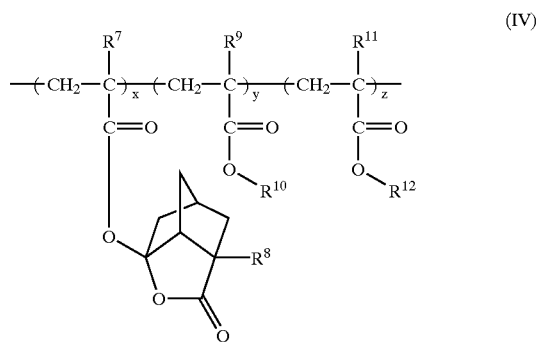

(IV)

The resin having the general formula (V) is described in Japanese Patent No.2856116, wherein $R^{13}$, $R^{14}$ and $R^{16}$ are hydrogen atom or methyl group, M is a group having a bridged cyclic hydrocarbon group having 7 to 13 carbon atoms, $R^{15}$ is a group decomposable by an acid, $R^{17}$ is a hydrogen atom or a hydrocarbon group having 1 to 12 carbon atoms, k, m and n are any numbers satisfying the relation of k+m+n=1, 0<k<1, 0<m<1 and 0≦n<1, and the weight average molecular weight of the polymer is 2000 to 200000.

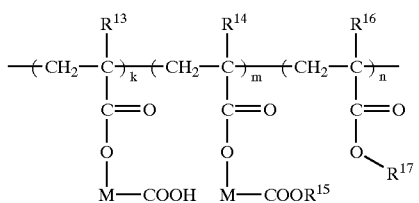

(V)

The resin having the general formula (VI) is described in Journal of Photopolymer Science and Technology, vol.10, no.4, p.545 to 550 (1997), wherein $R^{18}$ is a methyl group or an ethyl group, $R^{18}$ is a group having a lactone structure, a and b are any numbers satisfying the relation of $a+b=1$, $0<a<1$ and $0<b<1$, and the weight average molecular weight of the polymer is 2000 to 200000.

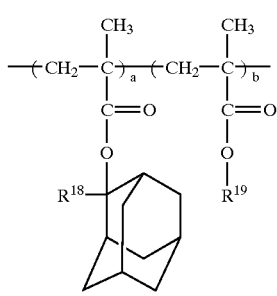

(VI)

The resin having the general formula (VII) is described in Journal of Photopolymer Science and Technology, vol.10, no.3, p.511 to 520 (1997), wherein c, d and e are any numbers satisfying the relation of $c+d+e=1$, $0<c<1$, $0<d<1$ and $0<e<1$, and the weight average molecular weight of the polymer is 2000 to 200000. The resins other than the positive resins described herein may be used so long as they have similar high transparency and reactivity.

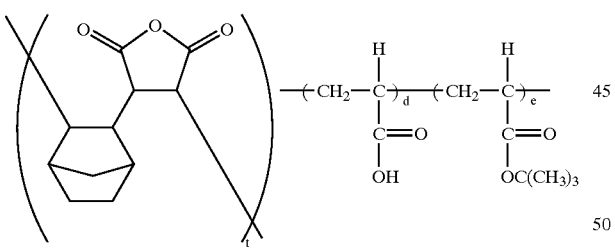

(VII)

In the negative photoresist composition, the resin is suitably used which is highly transparent to the ray having the wavelength of the exposing ray in the range from the far ultraviolet ray to the vacuum ultraviolet ray having a wavelength between 130 nm and 220 nm and may be insolubilized in an alkaline developing solution by the function of the acid. Ordinarily, 60 to 99.8 weight parts, preferably 70 to 99 weight parts of the resin with respect to 100 weight parts of the whole photoresist composition excluding the solvent is appropriate.

The resin preferably used in the negative photoresist composition of the present invention includes resins represented by the following general formulae (VIII) and (IX).

The resin having the general formula (VIII) is described in Journal of Photopolymer Science and it Technology, vol.12, no.3, p.487 to 492 (1999), wherein f, g and h are any numbers satisfying the relation of $f+g+h=1$, $0<f<1$, $0<g<1$ and $0<h<1$, and the weight average molecular weight of the polymer is 2000 to 200000.

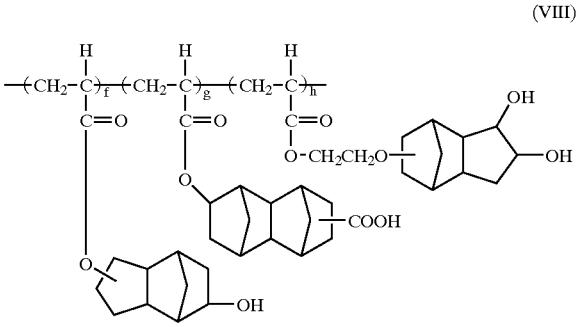

(VIII)

The resin has the general formula (IX) wherein q, r and s are any numbers satisfying the relation of $q+r+s=1$, $0<q<1$, $0<r<1$ and $0<s<1$, and the weight average molecular weight of the polymer is 2000 to 200000. The resins other than the negative resist resins described herein may be used so long as they have similar high transparency and reactivity.

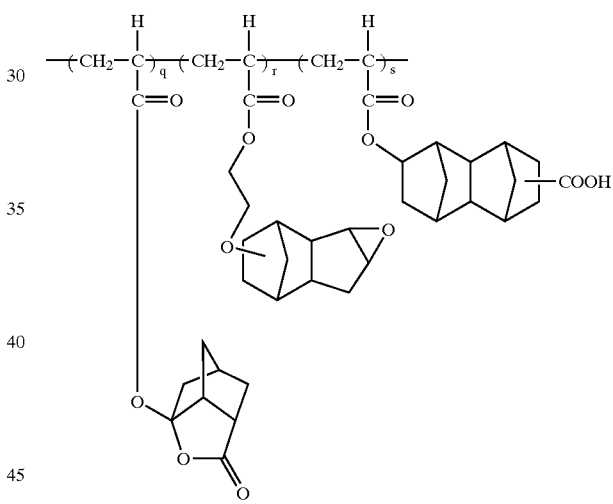

(IX)

A crosslinking agent for promoting an insolubilization reaction of the resin at the exposed portion may be added. An example of the preferable crosslinking agent includes a urea-melamine-based crosslinking agent such as hexamethoxymethyl-melamine, 1,3,4,6-tetrakis (methoxymethyl)glycoluril, 1,3-bis(methoxymethyl)-4,5-bis(methoxymethyl)-ethyleneurea and 1,3-bus (methoxymethyl)urea, and a polyvalent alcohol such as 2,3-dihydroxy-5-hydroxymethylnorborane, 1,4-cyclohexandimethanol and 3,4,8(9)-trihydroxytricyclodecane. The preferable crosslinking agent is not restricted thereto. A single crosslinking agent or a plurality of mixed crosslinking agents may be used.

The photoresist composition of the present invention contains a proper amount of the solvent in addition to the resin and the sulfonium salt compound. The solvent may be any organic solvent provided that it uniformly dissolves the components of the resin and the sulfonium salt compound and can form a uniform applied film by using the photoresist composition by means of a spincoat method. A single solvent or a plurality of mixed solvents may be used. A concrete example thereof includes an alcohol such as n-propyl alcohol, isoproryl alcohol, n-butyl alcohol and tert-butyl alcohol, an ester such as methylcellosolve acetate, ethylcellosolve acetate, proryleneglycol monoethylether acetate, methyl lactate, ethyl lactate, 2-methoxybutyl butyrate, 2-ethoxyethyl butyrate, methyl pyruvate, ethyl pyruvate, methyl 3-methoxy propionate and ethyl 3-methoxy propionate and, a cyclic ketone or alcohol such as N-methyl pyrrolidinone, cyclohexanone, cyclopentanone and cyclohexanol, and a keone such as methyl ethyl ketone and a glycol ether such as 1,4-dioxane, ethyleneglycol monomethyl ether, ethyleneglycol monomethyl ether acetate, ethyleneglycol monoethyl ether, ethyleneglycol monoisopropyl ether, diethyleneglycol monomethyl ether and diethyleneglycol dimethyl ether. The preferable solvent is not restricted thereto.

The fundamental components of the positive and the negative photoresist compositions of the present invention are the sulfonium salt compound having the general formula (I), the resin and the solvent. However, a dissolving inhibitor, a crosslinking agent, a basic compound, a surface-active agent, a pigment, a stabilizer, an application modifier and a dye may be added thereto depending on necessity.

A method for patterning of the present invention is to transfer a mask pattern on a photoresist applied film utilizing the positive or the negative photoresist composition and the exposing ray selected from 130 to 220 nm. In the method, the steps of applying the photoresist, and of baking the composition before and after the exposure are essentially the same as those of the patterning using the conventional chemically amplified photoresist. The acid catalyzed reaction by the protonic acid produced by the exposure is substantially the same as that employing a triphenylsulfonium salt compound as a photo-acid generator (sensitized agent).

EXAMPLES

The sulfonium salt compound, its preparation and the photoresist composition employing the sulfonium salt compound as a photo-acid generator will be described more in detail by Examples. The attainment of the high resolution in the method of patterning utilizing the photoresist composition will be also described by Examples. Although these Examples are preferable, the present invention is not restricted thereto.

Example 1

A sulfonium salt compound having the following general formula was synthesized in accordance with the following procedures. The compound is that of the above general formula (I) wherein X is a methylene group (—CH$_2$—), R$^1$ is a methyl group, R$^2$ is a cyclohexyl group, R$^3$, R$^4$, R$^5$ and R$^6$ are hydrogen atoms and Y$^-$ is a trifluoromethane sulfonate ion.

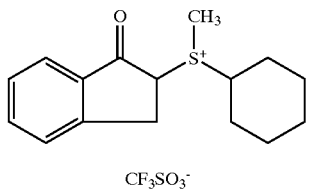

CF$_3$SO$_3^-$

After 5.5 g of cyclohexylmercaptan was dissolved into 50 ml of ethanol, 1.97 g of sodium hydroxide was added thereto and refluxed under heating. After the complete dissolving of the sodium hydroxide, the solution was cooled on standing. After 10 g of 2-bromo-1-indanone (available from Aldrich Corporation) dissolved in 10 ml of ether was added dropwise to the cooled solution and stirred for three hours at room temperature, the reaction mixture was poured into 300 ml of cold water. After 200 ml of ether was added thereto for extracting an organic phase, the ether layer was sequentially washed with an aqueous sodium chloride solution and water. After the ether layer was dried with magnesium sulfate, the ether was evaporated under vacuum. The residue was isolated and purified through a silica gel column (elute: hexane/ethyl acetate=9/1) to provide 2.4 g of 2-(cyclohexylthio)-1-indanone (yield: 23%). Then, 2 g of the 2-(cyclohexylthio)-1-indanone was dissolved into 6 ml of nitromethane, and 10.7 g of methyl iodide was added thereto and stirred at room temperature. After an hour, 40 ml of nitromethane dissolving 2.09 g of silver trifluoromethanesulfonate was added dropwise thereto. After the stirring for 18 hours at room temperature, precipitated silver iodide was filtrated and a filtrate was concentrated to about one-third under vacuum. After the residue was added dropwise to 250 ml of ether, a precipitated sulfonium salt was filtered. The precipitated sulfonium salt was recrystalized from ethyl acetate-ethanol to provide 2.42 g of the sulfonium salt having the above structure (yield: 73%).

Melting point: 122° C. $^1$H-NMR (CDCl$_3$): δ (ppm) 1.2 to 2.36 (10H, m), 2.97, 3.14 (3H, s), 3.62 (1H, dt), 3.88 to 4.31 (2H, m), 4.77 to 5.02 (1H, m), 7.4 to 7.88 (4H, m).

Example 2

A sulfonium salt compound having the following general formula was synthesized in accordance with the following procedures. The compound is that of the above general formula (I) wherein X is a methylene group (—CH$_2$—), R$^1$ is a cyclohexyl group, R$^2$ is a norbornyl group, R$^3$, R$^4$, R$^5$ and R$^6$ are hydrogen atoms and Y$^-$ is a trifluoromethane sulfonate ion.

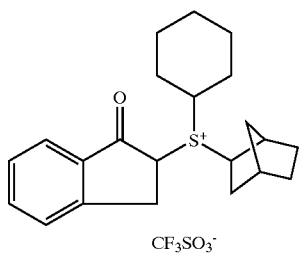

CF$_3$SO$_3^-$

In accordance with the procedures of Example 1, 2-(cyclohexylthio)-1-indanone was synthesized. Then, 2-bromonorbornane was used in place of the methyl iodide to prepare the target sulfonium salt (yield: 9%). Melting point: 99° C.

Example 3

A sulfonium salt compound having the following general formula was synthesized in accordance with the following procedures. The compound is that of the above general formula (I) wherein X is a methylene group (—CH$_2$—), R$^1$ and R$^2$ are methyl groups, R$^3$, R$^4$, R$^5$ and R$^6$ are hydrogen atoms and Y$^-$ is a trifluoromethane sulfonate ion.

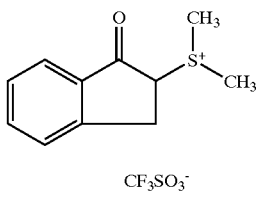

After 10 g of 2-bromo-1-indanone was dissolved into 50 ml of ethanol, 25 ml of a 15% aqueous solution of a sodium salt of methylmercaptan was added dropwise thereto. After stirring for 3 hours at room temperature, the reaction mixture was poured into 300 ml of cold water. After 200 ml of ether was added thereto for extracting an organic phase, the ether layer was sequentially washed with an aqueous sodium chloride solution and water. After the ether layer was dried with magnesium sulfate, the ether was evaporated under vacuum. The residue was isolated and purified through a silica gel column (elute: hexane/ethyl acetate=7/1) to provide 3.2 g of 2-(methylthio)-1-indanone (yield: 38%).

Then, 2 g of the 2-(methylthio)-1-indanone was dissolved into 10 ml of nitromethane, and 14 g of methyl iodide was added thereto and stirred at room temperature. After an hour, 60 ml of nitromethane dissolving 2.88 g of silver trifluoromethanesulfonate was added dropwise thereto. After the stirring for 16 hours at room temperature, precipitated silver iodide was filtrated and a filtrate was concentrated to about one-third under vacuum. After the residue was added dropwise to 200 ml of ether, a precipitated sulfonium salt was filtered. The sulfonium salt was dissolved into acetone and reprecipitated into ether. Then, the precipitate was recrystalized from ethyl acetate-ethanol to provide 2.95 g of the sulfonium salt having the above structure (yield: 80%).

Melting point: 132° C. $^1$H-NMR (THF-$d_8$): δ (ppm) 3.14 (3H, s), 3.20 (3H, s), 3.74 to 3.95 (2H, m), 4.87 to 5.02 (1H, m), 7.38 to 7.85 (4H, m).

Example 4

A sulfonium salt compound having the following general formula was synthesized in accordance with the following procedures. The compound is that of the above general formula (I) wherein X is a methylene group (—$CH_2$—), $R^1$ is an ethyl group, $R^2$ is a methyl group, $R^3$, $R^4$, $R^5$ and $R^6$ are hydrogen atoms and $Y^-$ is a trifluoromethane sulfonate ion.

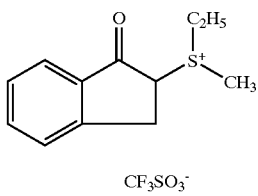

In accordance with the procedures of Example 3, 2-(methylthio)-1-indanone was synthesized. Then, bromonoethane was used in place of the methyl iodide to prepare the target sulfonium salt (yield: 14%). Melting point: 166° C.

Example 5

A sulfonium salt compound having the following general formula was synthesized in accordance with the following procedures. The compound is that of the above general formula (I) wherein X is a methylene group (—$CH_2$—), $R^1$ is a methyl group, $R^2$ is a norbornyl group, $R^3$, $R^4$, $R^5$ and $R^6$ are hydrogen atoms and $Y^-$ is a trifluoromethane sulfonate ion.

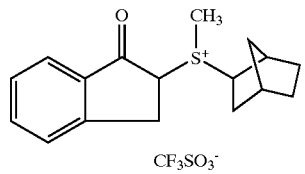

In accordance with the procedures of Example 3, 2-(methylthio)-1-indanone was synthesized. Then, 2-bromonorbornane was used in place of the methyl iodide to prepare the target sulfonium salt (yield: 48%). Melting point: 102° C.

$^1$H-NMR (CDCl$_3$): δ (ppm) 1.16 to 2.12 (8H, m), 2.26 to 2.76 (2H, m), 2.99, 3.13 (3H, s), 3.54 to 3.8 (1H, m), 3.84 to 4.34 (2H, m), 4.72 to 5.04 (1H, m), 7.41 to 7.9 (4H, m).

Example 6

A sulfonium salt compound having the following general formula was synthesized in accordance with the following procedures. The compound is that of the above general formula (I) wherein X is a methylene group (—$CH_2$—), $R^1$ and $R^2$ are a bivalent pentamethylene group (—$R^1$—$R^2$—) bonded to each other, $R^3$, $R^4$, $R^5$ and $R^6$ are hydrogen atoms and $Y^-$ is a bromide ion.

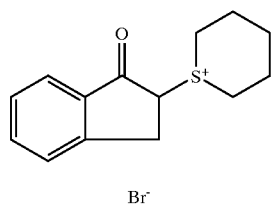

After 3.44 g of 2-bromo-1-indanone was dissolved in a mixed solution of 20 ml of acetone and 1 ml of water, 1.5 g of pentamethylene sulfide was added thereto and stirred for 4 days at room temperature. A precipitated sulfonium salt was filtered, dissolved into methanol and reprecipitated into ether for purification to prepare 1.75 g of the target sulfonium salt (yield: 38%).

Decomposition point: 122° C.

Example 7

A sulfonium salt compound having the following general formula was synthesized in accordance with the following procedures. The compound is that of the above general formula (I) wherein X is a methylene group (—$CH_2$—), $R^1$ and $R^2$ are a bivalent pentamethylene group (—$R^1$—$R^2$—) bonded to each other, $R^3$, $R^4$ and $R^6$ are hydrogen atoms, $R^5$ is a methoxy group and $Y^-$ is a bromide ion.

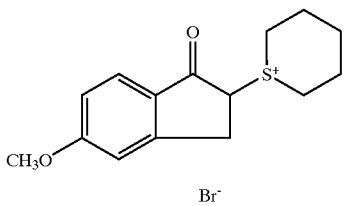

Br⁻

In accordance with the procedures of Example 6, the target sulfonium salt (yield: 30%) was synthesized by using 2-bromo-5-methoxy-1-indanone [W. S. Johnson, et al., J. Am. Chem. Soc., vol.66, p.218 to 220 (1944)] in place of the 2-bromo-1-indanone.

Decomposition point: 144° C.

Example 8

A sulfonium salt compound having the following general formula was synthesized in accordance with the following procedures. The compound is that of the above general formula (I) wherein X is a methylene group (—$CH_2$—), $R^1$ and $R^2$ are a bivalent pentamethylene group (—$R^1$—$R^2$—) bonded to each other, $R^3$, $R^4$, $R^5$ and $R^6$ are hydrogen atoms and $Y^-$ is a nonafluorobutanesulfonate ion.

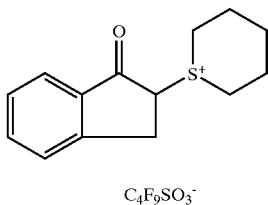

$C_4F_9SO_3^-$

After 1.5 g of the sulfonium salt obtained in Example 6 was dissolved into 12 ml of water, 50 ml of water dissolving 1.62 g of potassium nonafluorobutanesulfonate was added and stirred at room temperature. After 3 hours, a precipitated salt was filtered and washed with water. Then, the salt was dissolved into acetone and reprecipitated into ether, and a precipitated salt was filtered. Thereafter, the filtered salt was recrystalized from an ethyl acetate-ethanol mixed solution to prepare 1.72 g of the target sulfonium salt (yield: 67%).

Melting point: 175° C. $^1$H-NMR (acetone-$d_6$): δ (ppm) 1.7 to 1.96 (2H, m), 2.0 to 2.16 (2H, m), 2.29 to 2.53 (2H, m), 3.73 to 4.06 (6H, m), 25 5.21 (1H, dd), 7.5 to 7.89 (4H, m).

Example 9

A sulfonium salt compound having the following general formula was synthesized in accordance with the following procedures. The compound is that of the above general formula (I) wherein X is a methylene group (—$CH_2$—), $R^1$ and $R^2$ are a bivalent tetramethylene group (—$R^1$—$R^2$—) bonded to each other, $R^3$, $R^4$, $R^5$ and $R^6$ are hydrogen atoms and $Y^-$ is a bromide ion.

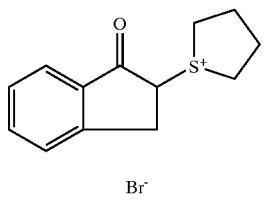

Br⁻

In accordance with the procedures of Example 6, the target sulfonium salt (yield: 33%) was synthesized by using tetrahydrothiophene in place of the pentamethylene sulfide.

Decomposition point: 116° C.

Example 10

A sulfonium salt compound having the following general formula was synthesized in accordance with the following procedures. The compound is that of the above general formula (I) wherein X is a methylene group (—$CH_2$—), $R^1$ and $R^2$ are a bivalent tetramethylene group (—$R^1$—$R^2$—) bonded to each other, $R^3$, $R^4$, $R^5$ and $R^6$ are hydrogen atoms and $Y^-$ is a nonafluorobutanesulfonate ion.

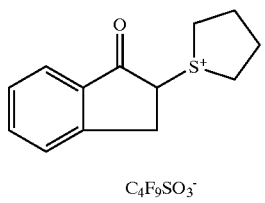

$C_4F_9SO_3^-$

At first, the sulfonium salt of Example 9 was synthesized. Thereafter, in accordance with the counter ion exchange reaction described in Example 8, the bromide ion was replaced with the nonafluorobutanesulfonate ion using potassium nonafluorobutanesulfonate to prepare the target sulfonium salt (yield: 40%).

Melting point: 156° C. $^1$H-NMR (acetone-$d_6$): δ (ppm) 2.35 to 2.71 (4H, m), 3.65 to 3.84 (1H, m), 4.18 to 4.35 (1H, m), 4.93 (1H, dd), 7.49 to 7.91 (4H, m).

Example 11

A sulfonium salt compound having the following general formula was synthesized in accordance with the following procedures. The compound is that of the above general formula (I) wherein X is a methylene group (—$CH_2$—), $R^1$ and $R^2$ are a bivalent tetramethylene group (—$R^1$—$R^2$—) bonded to each other, $R^3$, $R^4$, $R^5$ and $R^6$ are hydrogen atoms and $Y^-$ is a heptadecafluorooctanesulfonate ion.

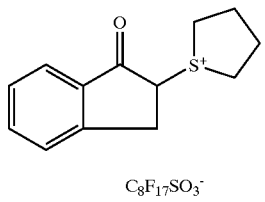

$C_8F_{17}SO_3^-$

At first, the sulfonium salt of Example 9 was synthesized. Thereafter, in accordance with the counter ion exchange reaction described in Example 8, the bromide ion was replaced with the heptadecafluorooctanesulfonate ion using potassium heptadecafluorooctanesulfonate to prepare the target sulfonium salt (yield: 32%).

Melting point: 145° C. $^1$H-NMR (acetone-d$_6$): δ (ppm) 2.35 to 2.71 (4H, m), 3.65 to 3.84 (1H, m), 4.18 to 4.35 (1H, m), 4.93 (1H, dd), 7.49 to 7.91 (4H, m).

Example 12

A sulfonium salt compound having the following general formula was synthesized in accordance with the following procedures. The compound is that of the above general formula (I) wherein X is a methylene group (—CH$_2$—), $R^1$ and $R^2$ are methyl groups, $R^3$, $R^4$, and $R^6$ are hydrogen atoms, $R^5$ is a methoxy group, and $Y^-$ is a trifluoromethanesulfonate ion.

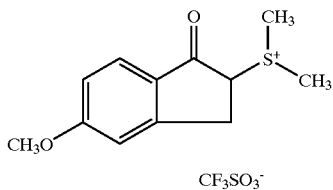

After 5 g of 2-bromo-5-methoxy-1-indanone [W. S. Johnson, et al., J. Am. Chem. Soc., vol.66, p.218 to 220 (1944)] was dissolved into 30 ml of acetone, 1.29 g of dimethyl sulfide was added thereto and stirred for 7 days at room temperature, and a precipitated salt was filtered. The salt was dissolved into methanol and reprecipitated into ether to provide 1.73 g of a bromide salt (yield: 28%). After 1.5 g of the bromide salt was dissolved into 10 ml of water, 5 ml of water dissolving 0.931 g of potassium trifluoromethane sulfonate was added dropwise thereto, and stirred for 2 hours at room temperature. After a precipitated salt was filtered and reprecipitated into acetone-ethanol for purification, the precipitate was recrystalized from an ethyl acetate-ethanol mixed solution to prepare 0.83 g of the target sulfonium salt (yield: 45%).

Melting point: 135° C.

Example 13

A sulfonium salt compound having the following general formula was synthesized in accordance with the following procedures. The compound is that of the above general formula (I) wherein X is —OCH$_2$—, $R^1$ and $R^2$ are methyl groups, $R^3$, $R^4$, $R^5$ and $R^6$ are hydrogen atoms, and $Y^-$ is a trifluoromethanesulfonate ion.

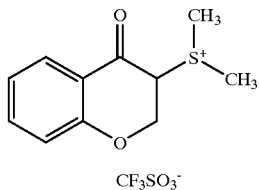

After 10.4 g of 3-bromo-4-chromanone [synthesized in accordance with procedures described in W. S. Johnson, et al., J. Am. Chem. Soc., vol.66, p.218 to 220 (1944)] was dissolved into 41.3 ml of ethanol, 21.3 ml of a 15% aqueous solution of a sodium salt of methylmercaptan was added dropwise thereto. After the stirring for 2 hours at room temperature, the reaction mixture was poured into 300 ml of cold water. An organic layer was extracted with 200 ml of ether, and the ether layer was sequentially washed with a sodium chloride aqueous solution and water. After the ether layer was dried with magnesium sulfate, the solvent was removed by evaporated under vacuum. The residue was isolated and purified through a silica gel column (elute: hexane/ethyl acetate=3/1) to provide 1.52 g of 3-methylthio-4-chromanone (yield: 17%).

Then, 1.48 g of the 3-methylthio-4-chromanone was dissolved into 8 ml of nitromethane, and 9.73 g of methyl iodide was added thereto and stirred at room temperature. After an hour, 40 ml of nitromethane dissolving 1.958 g of silver trifluoromethanesulfonate was added dropwise thereto. After the stirring for 20 hours at room temperature, precipitated silver iodide was filtrated and a filtrate was concentrated to about one-third under vacuum. After the residue was added dropwise to 200 ml of ether, a precipitated sulfonium salt was filtered. The sulfonium salt was dissolved into acetone and reprecipitated into ether. Then, the precipitate was recrystalized from ethyl acetate-ethanol to provide 1.77 g of the sulfonium salt having the above structure (yield: 65%).

Melting point: 113° C.

Example 14

A sulfonium salt compound having the following general formula was synthesized in accordance with the following procedures. The compound is that of the above general formula (I) wherein X is an ethylene group (—C$_2$H$_4$—), $R^1$ and $R^2$ are methyl groups, $R^3$, $R^4$ and $R^6$ are hydrogen atoms, $R^5$ is a methoxy group, and $Y^-$ is a trifluoromethanesulfonate ion.

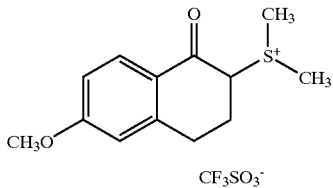

After 20 g of 2-bromo-6-methoxy-1-tetralone [synthesized in accordance with procedures described in W. S. Johnson, et al., J. Am. Chem. Soc., vol.66, p.218 to 220 (1944)] was dissolved into 100 ml of tetrahydrofuran, 36.5 g of a 15% aqueous solution of a sodium salt of methylmercaptan was added dropwise thereto. After the stirring for 3 hours at room temperature, the reaction mixture was poured into 300 ml of cold water. An organic layer was extracted with 200 ml of ether, and the ether layer was sequentially washed with a sodium chloride aqueous solution and water. After the ether layer was dried with magnesium sulfate, the solvent was removed by evaporated under vacuum. The residue was dissolved into 320 ml of a mixed solvent of hexane/ethyl acetate (7/1), and silica gel was added thereto for adsorbing impurities. After the silica gel was removed by filtration, the filtrate was concentrate under vacuum to provide 11.06 g of 6-methoxy-2-(methylthio)-1-tetralone (yield: 64%).

Then, 4 g of the 6-methoxy-2-(methylthio)-1-tetralone was dissolved into 20 ml of nitromethane, and 22.99 g of methyl iodide was added thereto and stirred at room temperature. After an hour, 100 ml of nitromethane dissolving 4.623 g of silver trifluoromethanesulfonate was added dropwise thereto. After the stirring for 16 hours at room temperature, precipitated silver iodide was filtrated and a filtrate was concentrated to about one-third under vacuum. After the residue was added dropwise to 200 ml of ether, a precipitated sulfonium salt was filtered. The sulfonium salt was dissolved into acetonitrile and reprecipitated into ether.

Then, the precipitate was recrystalized from ethyl acetate-acetonitrile to provide 4.09 g of the sulfonium salt having the above structure (yield: 59%).

Melting point: 130° C. $^1$H-NMR (acetone-$d_6$): δ (ppm) 2.49 to 2.63 (1H, br), 3.12 to 3.17 (3H, m), 3.29 (6H, s), 3.93 (3H, s), 5.28 (1H, dd), 6.9 to 7.07 (2H, m), 7.96 (1H, d).

Example 15

A sulfonium salt compound having the following general formula was synthesized in accordance with the following procedures. The compound is that of the above general formula (I) wherein X is an ethylene group (—$C_2H_4$—), $R^1$ and $R^2$ are methyl groups, $R^3$, $R^4$ and $R^6$ are hydrogen atoms, $R^5$ is a methoxy group, and $Y^-$ is a nonafluorobutanesulfonate ion.

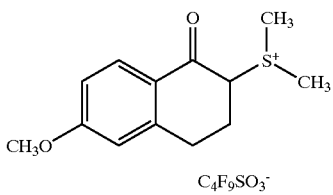

After 4.628 g of the 6-methoxy-2-(methylthio)-1-tetralone was dissolved into 30 ml of acetonitrile, 10 ml of acetonitrile dissolving 6.54 g of methyl nonafluorobutanesulfonate was added dropwise thereto under ice cooling. After the mixture was kept in a refrigerator overnight, it was poured into 250 ml of ether, and a precipitated salt was filtered. Then, the salt was dissolved into acetonitrile and reprecipitated into ether, and a precipitated salt was filtered. Thereafter, the filtered salt was recrystalized from an ethyl acetate-acetonitrile mixed solvent to prepare 6.33 g of the target sulfonium salt (yield: 57%).

Melting point: 143° C. $^1$H-NMR (acetone-$d_6$): δ (ppm) 2.49 to 2.63 (1H, br), 3.12 to 3.17 (3H, m), 3.29 (6H, s), 3.93 (3H, s), 5.28 (1H, dd), 6.9 to 7.07 (2H, m), 7.96 (1H, d).

Example 16

Evaluation of Transparency of Sulfonium Salts

The evaluation of the transparency of the sulfonium salt compounds of the above Examples in a range from a far ultraviolet ray to a vacuum ultraviolet ray having a wavelength between 130 nm and 220 nm was conducted.

After 3.1 mg of the sulfonium salt obtained in. Example 1 was dissolved into 25 ml of acetonitrile, an absorption spectrum was measured using an ultraviolet visible ray spectrophotometer (UV-365 available from Shimazu Seisakusho K.K.) and utilizing a quartz cell having a light path length of 1 mm and the acetonitrile solution. A molar absorption coefficient at 193.4 nm (wavelength of ArF ray) was calculated from the measured absorbance. Similarly, molar absorption coefficients of the sulfonium salts obtained in Examples 3, 4, 8, 10, 13 and 14, and of triphenylsulfonium trifluoromethane sulfonate (TPS-105 available from Midori Kagaku K.K.) were also calculated. The measured molar absorption coefficients are shown in Table 1. As shown therein, the absorptions of the ArF ray of the sulfonium salts of the Examples are smaller than that of the conventional triphenylsulfonium salt, and the sulfonium salts of the Examples have more excellent transparency.

TABLE 1

| Sulfonium Salt Compound | Molar Absorption Coefficient (1 · mol$^{-1}$ · cm$^{-1}$) |
|---|---|
| Sulfonium Salt of Example 1 | 16980 |
| Sulfonium Salt of Example 3 | 16052 |
| Sulfonium Salt of Example 4 | 17479 |
| Sulfonium Salt of Example 8 | 16441 |
| Sulfonium Salt of Example 10 | 17419 |
| Sulfonium Salt of Example 14 | 14149 |
| TPS: $(C_6H_5)_3S^+$ $CF_3SO_3^-$ | 54230 |

Example 17

Evaluation of Patterning of Positive Resist by Using Sulfonium Salts

A resist including (a) resin, (b) photo-acid generator and (c) solvent was prepared.

(a) Resin: 2 g of the resin having the following general formula.

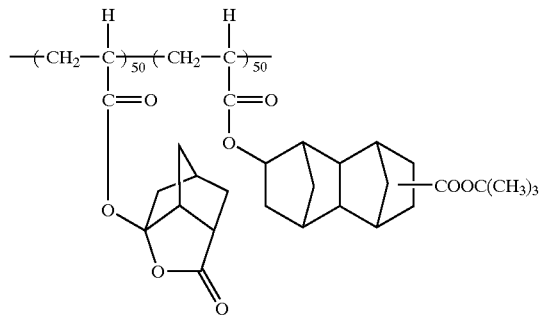

(b) Photo-acid generator: 0.02 g of the sulfonium salt obtained in Example 3.

(c) Solvent: 11.5 g of propyleneglycol monomethyl ether acetate.

After the three components were mixed, the mixture was filtered through a polytetrafluoroethylene filter having an aperture of 0.2 μm to prepare the resist. After the resist was applied to a 4-inch silicon substrate by means of spin-coating, the substrate was baked on a hotplate for a minute at 130° C. to form a thin film having a thickness of 0.4 μm. Then, the wafer having the coated resist was placed in a tightly sealed light exposing experimental device sufficiently purged with nitrogen.

After a mask prepared by depicting a pattern with chromium on a quartz plate was adhered on the resist film, the ray from an ArF excimer laser was irradiated on the resist film through the mask. Immediately thereafter, the plate was baked on a hotplate for 60 seconds at 110° C., and the resist was developed for 60 seconds by a dipping method in a 2.38% TMAH [$(CH_3)_4NOH$] aqueous solution at 23° C., followed by rinsing with pure water for 60 seconds. As a result, a positive pattern was obtained after only the exposed portion of the resist film was dissolved in the developing agent and removed. Similarly, the resists using the sulfonium salts obtained in Examples 10, 13 and 14 and the triphenylsulfonium trifluoromethane sulfonate (TPS, Comparative Example) as the photo-acid generator were also evaluated. The sensitivities and the resolutions of the resists are shown in Table 2. As shown therein, the positive photoresists of Examples have more excellent resolution characteristics.

TABLE 2

| Photo-acid Generator | Resolution (μm · L/S) | Sensitivity (mJ/cm²) |
|---|---|---|
| Sulfonium Salt of Example 3 | 0.18 | 6 |
| Sulfonium Salt of Example 10 | 0.17 | 6.5 |
| Sulfonium Salt of Example 13 | 0.17 | 5.5 |
| Sulfonium Salt of Example 14 | 0.17 | 5.5 |
| TPS: $(C_6H_5)_3S^+ CF_3SO_3^-$ | 0.19 | 6.5 |

Example 18
Evaluation of Patterning of Negative Resist by Using Sulfonium Salts

A resist including (a) resin, (b) photo-acid generator, (c) crosslinking agent and (d) solvent was prepared.

(a) Resin: 2 g of the resin having the following general formula.

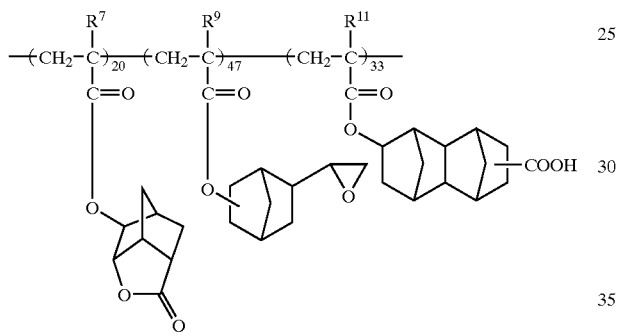

(b) Photo-acid generator: 0.04 g of the sulfonium salt obtained in Example 3.
(c) Crosslinking agent: 0.3 g of 2,3-dihydroxy-5-hydroxymethylnorbornane
(d) Solvent: 11.5 g of ethyl lactate After the four components were mixed, the mixture was filtered through a polytetrafluoroethylene filter having an aperture of 0.2 μm to prepare the resist. After the resist was applied to a 4-inch silicon substrate by means of spin-coating, the substrate was baked on a hotplate for a minute at 80° C. to form a thin film having a thickness of 0.4 μm. Then, the wafer having the coated resist was placed in a tightly sealed light exposing experimental device sufficiently purged with nitrogen.

After a mask prepared by depicting a pattern with chromium on a quartz plate was adhered on the resist film, the ray from an ArF excimer laser was irradiated on the resist film through the mask. Immediately thereafter, the plate was baked on a hotplate for 60 seconds at 130° C., and the resist was developed for 60 seconds by a dipping method in a 2.38% TMAH aqueous solution at 23° C., followed by rinsing with pure water for 60 seconds. As a result, a negative pattern was obtained after only the non-exposed portion of the resist film was dissolved in the developing agent and removed. Similarly, the resists using the sulfonium salts obtained in Examples 10, 13 and 14 and the triphenylsulfonium trifluoromethane sulfonate (TPS) as the photo-acid generator were also evaluated. The sensitivities and the resolutions of the resists are shown in Table 3. As shown therein, the negative photoresists of Examples have more excellent resolution characteristics.

TABLE 3

| Photo-acid Generator | Resolution (μm · L/S) | Sensitivity (mJ/cm²) |
|---|---|---|
| Sulfonium Salt of Example 3 | 0.18 | 5 |
| Sulfonium Salt of Example 10 | 0.17 | 6 |
| Sulfonium Salt of Example 13 | 0.18 | 4.5 |
| Sulfonium Salt of Example 14 | 0.18 | 4.5 |
| TPS: $(C_6H_5)_3S^+ CF_3SO_3^-$ | 0.19 | 6.8 |

Since the above embodiments are described only for examples, the present invention is not limited to the above embodiments and various modifications or alternations can be easily made therefrom by those skilled in the art without departing from the scope of the present invention.

What is claimed is:
1. A positive photoresist material comprising:
   a sulfonium salt compound acting as a photo-acid generator, the sulfonium salt compound being designated by a general formula (I),

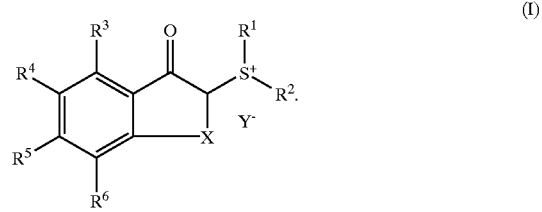

(I)

wherein $R^1$ and $R^2$ are independently selected from the group consisting of a linear alkyl group, a branched alkyl group, a monocyclic alkyl group and a cross-linked cyclic alkyl group, or $R^1$ and $R^2$ having the saturated alkyl group are linked to each other forming a ring or $R^1$ and $R^2$ are linked to each other forming a ring having a substituted oxo group,
   $R^3$, $R^4$, $R^5$ and $R^6$ are independently selected from the group consisting of a hydrogen atom, a halogen atom, an alkyl group and an alkoxy group having 1 to 4 carbon atoms,
   X is selected from the group consisting of —CH₂—, —C₂H₄— and —OCH₂— (wherein an oxy group is bonded to a benzene ring), and
   Y⁻ is a counter ion.
2. The photoresist material as defined in claim 1, wherein the counter ion designated by the Y⁻ is an anionic component selected from the group consisting of a perfluoroalkyl-sulfonate ion designated by a general formula (II) (wherein "m" is a positive integer from 1 to 9)

(II), an alkylsulfonate ion, benzenesulfonate ion, alkylbenzene-sulfonate ion, fluorine-substituted benzenesulfonate ion, fluorine-substituted alkylbenzenesulfonate ion, an ion designated by a general formula (III)

(III), (wherein "k" is a positive integer from 1 to 9), $BF_4^-$, $AsF_6^-$, $SbF_6^-$, $PF_6^-$, $Br^-$ and $I^-$.

3. A method comprising the steps of:
forming a photoresist layer by application of the sulfonium salt compound as defined in claim 1 as a positive photoresist material or a negative photoresist material on an underlying layer to be patterned;
transferring a desired pattern to the photoresist film on a photoresist composition by exposing the photoresist layer to light having a wavelength between 130 and 220 nm;
baking the photoresist layer: and
developing the photoresist layer to form a photoresist pattern.

4. The method as defined in claim 3, wherein the light from an ArF excimer laser is used as the light for exposing.

5. The method as defined in claim 3, wherein the light from an $F_2$ excimer laser is used as the light for exposing.

6. A negative photoresist material comprising:
a sulfonium salt compound acting as a photo-acid generator, the sulfonium salt compound being designated by a general formula (I),

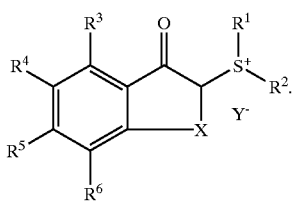

(I)

wherein $R^1$ and $R^2$ are independently selected from the group consisting of a linear alkyl group, a branched alkyl group, a monocyclic alkyl group and a cross-linked cyclic alkyl group, or $R^1$ and $R^2$ having the saturated alkyl group are linked to each other forming a ring or $R^1$ and $R^2$ are linked to each other forming a ring having a substituted oxo group, $R^3$, $R^4$, $R^5$ and $R^6$ are independently selected from the group consisting of a hydrogen atom, a halogen atom, an alkyl group and an alkoxy group having 1 to 4 carbon atoms, X is selected from the group consisting of —$CH_2$—, —$C_2H_4$— and —$OCH_2$— (wherein an oxy group is bonded to a benzene ring), and $Y^-$ is a counter ion.

7. The photoresist material as defined in claim 6, wherein the counter ion designated by the $Y^-$ is an anionic component selected from the group consisting of a perfluoroalkylsulfonate ion designated by a general formula (II) (wherein "m" is a positive integer from 1 to 9)

$$C_mF_{2m+1}SO_3^-  \quad (II)$$

an alkylsulfonate ion, benzenesulfonate ion, alkylbenzenesulfonate ion, fluorine-substituted benzenesulfonate ion, fluorine-substituted alkylbenzenesulfonate ion, an ion designated by a general formula (III)

$$C_kH_{2k+1}SO_3^- \quad (III),$$

(wherein "k" is a positive integer from 1 to 9), $BF_4^-$, $AsF_6^-$, $SbF_6^-$, $PF_6^-$, $Br^-$ and $I^-$.

* * * * *